United States Patent [19]
Horiuchi et al.

[11] Patent Number: 5,260,197
[45] Date of Patent: Nov. 9, 1993

[54] L-FUCOSE DEHYDROGENASE, A PROCESS FOR PRODUCTION THEREOF, QUANTITATIVE ASSAY FOR L-FUCOSE USING SAID ENZYME AND A KIT FOR QUANTITATIVE ASSAY

[75] Inventors: Tatsuo Horiuchi, Nagareyama; Minoru Hiruma, Kasukabe; Toshiyuki Suzuki, Noda, all of Japan

[73] Assignee: Noda Institute for Scientific Research, Chiba, Japan

[21] Appl. No.: 407,148

[22] Filed: Sep. 14, 1989

[30] Foreign Application Priority Data

Sep. 21, 1988 [JP] Japan .................. 63-234745

[51] Int. Cl.⁵ ............................ C12Q 1/32
[52] U.S. Cl. .............................. 435/26; 435/18; 435/25; 435/189; 435/190
[58] Field of Search ............. 435/25, 26, 18, 190, 435/189; 436/94, 93

[56] References Cited

PUBLICATIONS

Iijima et al., J. Biochem., 70, 75–78 (1971).
Biosis Abstract No. 69057371, Endo et al., J. Biochem (Tokyo), 86(5), 1979, pp. 1559–1566.
H. Schauchter, J. Sarney, E. J. McGuire, and S. Roseman, J. Bio. Chem., vol. 244, No. 17, pp. 4785–4792 (Sep. 1969).
Patrick Wm. Mobley and Robert P. Metzger, Arch. Biochem. Biophys., vol. 186, No. 1, pp. 184–188 (Feb. 1978).
N. J. Mello de Souza, M. F. Guimaraes and L. A. Veiga, Arg. Biol. Technol., vol. 30, pp. 361–366 (Jun. 1987).
Agric, Biol. Chem., vol. 39(11), 2227–2234 (1975).
J. E. Mrochek, S. R. Dinsmore, D. C. Tormey, and T. P. Waalkes, Clin. Chem., vol. 22, No. 9, pp. 1516–1521 (1976).
John B. Morris, Anal. Biochem., vol. 121, pp. 129–134 (1982).
Menashi A. Cohenford, Joseph C. Urbanowski and Joel A. Dain, Anal. Biochem., vol. 112, pp. 76–81 (1981).
John B. Morris, Methods Enzym. Anal. (3rd Ed.), vol. 6, pp. 386–398

Primary Examiner—Amelia Burgess Yarbrough
Attorney, Agent, or Firm—Banner, Birch, McKie & Beckett

[57] ABSTRACT

L-Fucose dehydrogenase having the following Physicochemical properties (1) and (2):
(1) Action and substrate specificity
It withdraws hydrogen from L-fucose and converts into L-fuconolactone and at the same time, reduces coenzyme $NADP^+$ to NADPH.
(2) pH and stable pH range
When Tris-imidazole-sodium acetate buffer solution is used, the optimum pH is in a range of 9.0 to 10.0 and the stable pH range is between 8.0 and 10.5.

The L-fucose dehydrogenase utilizing $NADP^+$ as coenzyme can be obtained by culturing L-fucose dehydrogenase-producing strain belonging to the genus Pseudomonas in a medium and collecting formed L-fucose dehydrogenase from the culture.

L-Fucose can be quantitatively determined by reacting a sample containing L-fucose with L-fucose dehydrogenase requiring $NADP^+$ as coenzyme and assaying NADPH produced.

6 Claims, 3 Drawing Sheets

L-FUCOSE DEHYDROGENASE, A PROCESS FOR PRODUCTION THEREOF, QUANTITATIVE ASSAY FOR L-FUCOSE USING SAID ENZYME AND A KIT FOR QUANTITATIVE ASSAY

BACKGROUND OF THE INVENTION

1. Field of the Invention

The present invention relates to a novel L-fucose dehydrogenase (hereafter referred to as L-FDH) which acts on L-fucose to produce L-fuconolactone and at the same time, converts oxidized nicotinamide adenine dinucleotide phosphate (NADP+) into reduced nicotinamide adenine dinucleotide (NADPH), a process for production thereof, a method for enzymatically assaying L-fucose using L-FDH and a kit for the quantitative assay.

2. Description of the Prior Art

It was pointed out that complex carbohydrates or glycoconjugates bound to proteins or lipids took a part in information transfer of the living body. Since then, findings on these sugars are rapidly increasing. In these findings, there is a report that L-fucose increases or decreases depending upon pathological conditions of lung cancer [Clin. Chem., vol. 22, No. 9, 1516-1521 (1976)]. It is thus expected that determination of this sugar would give useful information on pathological conditions of the patient with lung cancer.

In order to determine L-fucose, a method using an enzyme is excellent in accuracy and simplicity. As enzymes for quantitative determination of L-fucose, there are known L-FDH of pork liver origin [J. Biol. Chem., Vol. 244, 4785-4792 (1969)], L-FDH of sheep liver origin [Arch. Biochem. Biophys., Vol. 186, 184-188 (1978)], L-FDH of rabbit liver origin [J. Biochem., Vol. 86, 1559-1565 (1979)], L-FDH derived from bacteria belonging to the genus Corynebacterium (Japanese Patent Application Kokai (Laid-Open) No. 62-155085), L-FDH derived from Pullularia pullulans [Arq. Biol. Tecnol., Vol. 30, 361-366 (1987)] and the like. These enzymes are all dehydrogenasses utilizing nicotinamide adenine dinucleotide (NAD+) as coenzyme.

Several attempts to quantitatively determine L-fucose using these enzymes have also been proposed in, for example, Japanese Patent Application Kokai (Laid-Open) No. 62-175197, Anal. Biochem., Vol. 121, 129-134 (1982), Anal. Biochem., Vol. 112, 76-81 (1981), Methods Enzym. Anal. (3rd Ed.), Vol. 6, 387-398, etc.

Where a part of the living body, for example, serum or the like is used as a sample and its component is enzymatically assayed, as a matter of course, it is desired to design the assay system in such a fashion that enzymes or metabolites in the metabolic systems naturally contained in the living body are minimized as less as possible.

From this viewpoint, the use of dehydrogenase utilizing NADP+ as coenzyme for assay is superior to the use of dehydrogenase utilizing NAD+ as coenzyme. This is because that enzymes (e.g., lactate dehydrogenase, etc.) utilizing NAD (or NADH) are contained in serum and the like in relatively large quantities and their metabolites (e.g., pyruvate, lactate, etc.) are always contained therein and hence, the NAD+ quantitative assay system tends to be readily affected by these compounds.

SUMMARY OF THE INVENTION

The present inventors have made investigations on a method for assaying L-fucose in a simple manner with high accuracy. As a result, it has been found that a bacterium belonging to the genus Pseudomonas isolated from soil could produce a novel enzyme which acts on L-fucose to produce L-fuconolactone and at the same time, converts NADP+ into NADPH and that the enzyme can be effectively utilized for assay of L-fucose. The present invention has thus been attained.

That is, the present invention is directed to a novel enzyme L-FDH which acts on L-fucose to produce L-fuconolactone and at the same time, converts NADP+ into NADPH. The present invention is also directed to a process for producing L-FDH utilizing NADP+ as coenzyme which comprises culturing a L-FDH-producing strain belonging to the genus Pseudomonas in a medium and collecting formed L-FDH from the culture.

The present invention is further directed to a method for quantitative determination of L-fucose which comprises reacting an L-fucose-containing sample with L-FDH utilizing NADP+ as coenzyme and determining NADPH produced. The present invention is also directed to a method for quantitative determination of bound L-fucose which comprises reacting an L-fucose-containing sample with L-fucosidase and L-FDH sequentially or simultaneously and assaying NADPH produced. The present invention is further directed to a kit for quantitative determination of L-fucose comprising at least said L-FDH, NADP+ and a buffer solution.

DESCRIPTION OF THE PREFERRED EMBODIMENTS

Hereafter the present invention is described in detail.
The physicochemical properties of novel enzyme L-FDH in the present invention are as follows.

(1) Action and substrate specificity

As shown in the following reaction equation, the enzyme oxidizes L-fucose to L-fuconolactone in the presence of L-fucose and NADP+ and at the same time reduces NADP+ to NADPH.

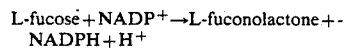

The enzyme shows the highest specificity (100%) to L-fucose but also reacts with L-galactose (96%) and D-arabinose (1%), etc. However, the enzyme hardly or does not act on other sugars at all that are ordinarily present.

Furthermore, the enzyme requires NADP+ (100%) as coenzyme but reacts very little with NAD+ (1%).

(2) Optimum pH and stable pH range

Figure 1:
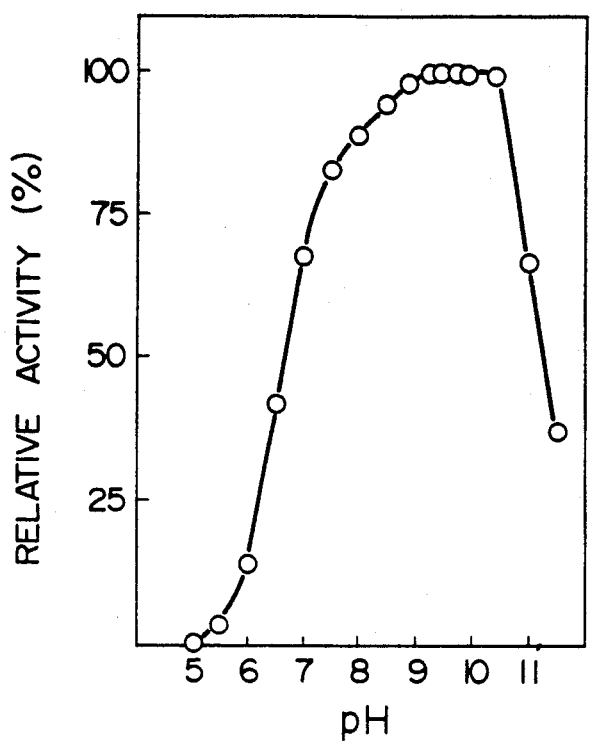
FIG. 1 is a graph showing the optimum pH of the present enzyme.
Figure 2:
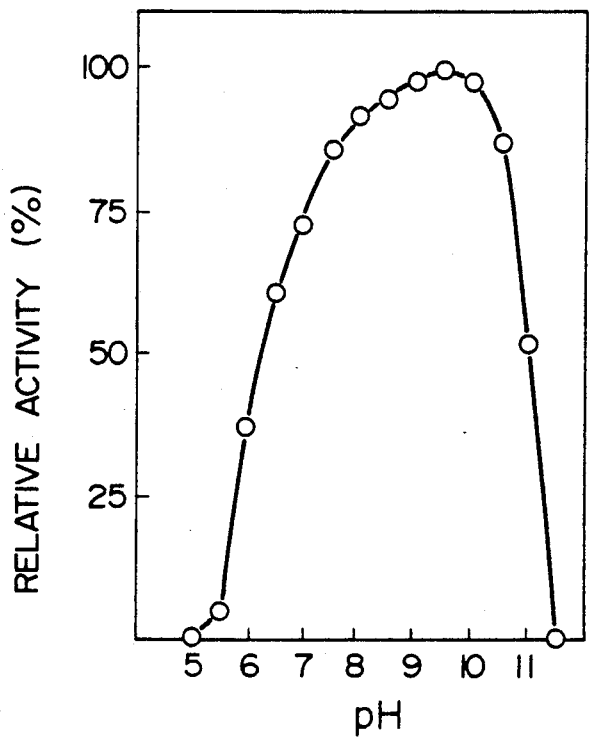
FIG. 2 is a graph showing the stable pH range.

When Tris-imidazole-sodium acetate buffer solution is used, the optimum pH is in a range of 9.0 to 10.0 as shown in FIG. 1. The stable pH range is between 8.0 and 10.5, as shown in FIG. 2.

(3) Optimum temperature range

Figure 3:
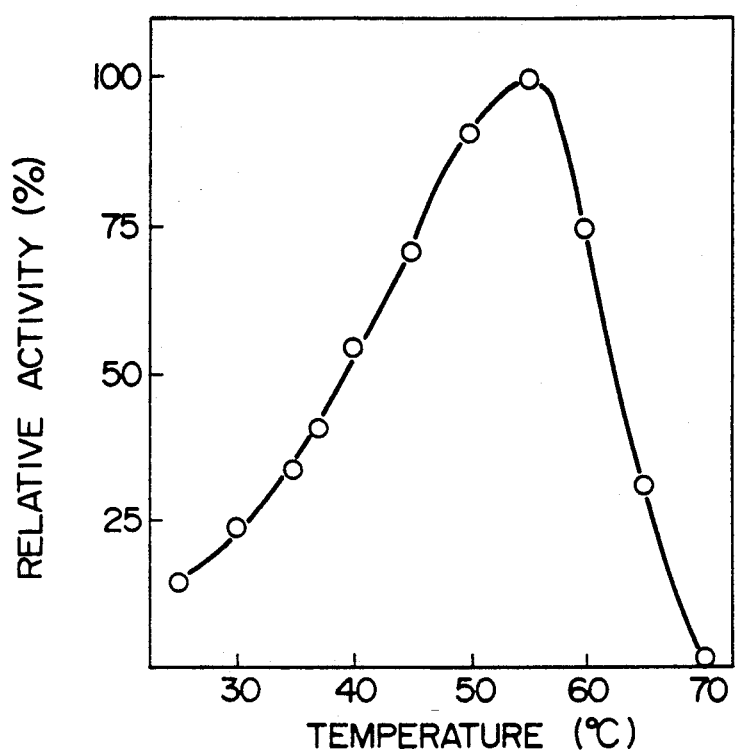
FIG. 3 is a graph showing the optimum temperature range of this enzyme and FIG. 4 is a graph showing thermal stability of the enzyme.

As shown in FIG. 3, the optimum temperature range is between 40° and 60° C.

(4) Conditions for inactivation by pH, temperature, etc.

Figure 4:
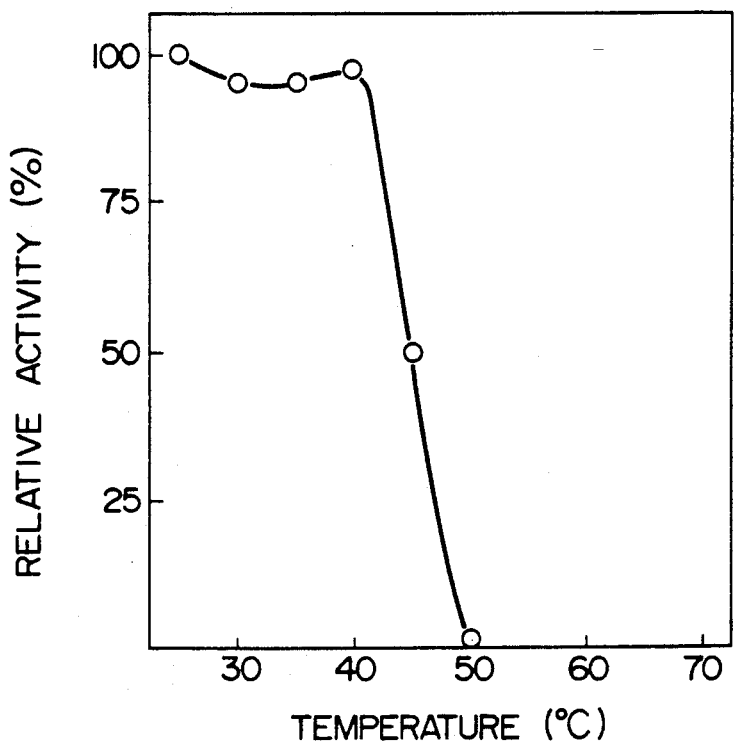

As shown in FIG. 4, the enzyme is stable up to 40° C. by heat treatment for 10 minutes but is rapidly inactivated at a higher temperature. By heat treatment at 30° C. for 60 minutes, the enzyme is stable at a pH value of 8.0 to 10.5 but is unstable at a pH value below 6.0.

(5) Influence of inhibitor and stabilization

| Inhibitor | Residual Activity (%) |
|---|---|
| None | 100 |
| $HgCl_2$ | 2 |
| $CdSO_4$ | 2 |
| $ZnSO_4$ | 81 |
| PCMB | 18 |
| Iodoacetamide | 91 |

The above table shows the results obtained when enzyme activity was measured in a reaction solution containing various metal salts and inhibitors in a concentration of 2 mM.

n and activation with $CaCl_2$, $MgSO_4$, $NiSO_4$, $CuSO_4$, EDTA, o-phenanthroline, $\alpha,\alpha'$-dipyridyl, KCN, $NaN_3$, etc. were not observed.

(6) Purification

The enzyme is isolated and purified in a conventional manner. Purification means such as precipitation with ammonium sulfate, column chromatography using Phenyl-Sepharose, column chromatography using DEAE Sephadex, gel filtration using Sephadex G-100, etc. are used singly or in an appropriate combination.

(7) Molecular weight

The molecular weight was determined by gel filtration through Sephadex G-100 column using 0.05 M potassium phosphate buffer solution (containing 0.1 M NaCl) and found to be approximately 32,000 to 36,000.

(8) Polyacrylamide gel electrophoresis

Figure 5:
FIG. 5 shows a band in electrophoresis.

Electrophoresis was performed in a conventional manner using 15% polyacrylamide gel. As the result, substantially a single band was observed as shown in FIG. 5. When bromophenol blue was used as an index, a relative mobility distance was 0.79 in the case of 7.5% gel, 0.57 in the case of 10% gel and 0.37 in the case of 15% gel.

(9) Isoelectric point

The isoelectric point determined by polyacrylamide gel isoelectrofocusing was found to be 5.2.

(10) Determination of activity

To 2.5 ml of Tris-imidazole-sodium acetate buffer solution (solution containing 0.12 M each is adjusted to pH of 9.5 with 4 N NaOH) is added 0.2 ml of 15 mM $NADP^+$ solution After keeping at 37° C. for 5 minutes, 0.1 ml of an enzyme solution is added and 0.2 ml of 150 mM L-fucose solution is further added to the system to initiate the reaction. Immediately thereafter, the reaction mixture is transferred to a cell for measurement of absorbance (1 cm light path) kept at 37° C. and absorbance is measured at the wavelength of 340 nm for 2 minutes or, if necessary, over a longer time period. One unit is an amount of enzyme that produces 1 $\mu$mole of NADPH for one minute.

As described above, the enzyme is novel L-FDH that was hitherto unknown in that $NADP^+$ is used as its coenzyme.

Next, a process for producing novel enzyme L-FDH in accordance with the present invention is described below.

A microorganism used is a strain belonging to the genus Pseudomonas and capable of producing L-FDH. A specific example is Pseudomonas sp. No. 1143. Variants and mutants of this strain may also be used. Pseudomonas sp. No. 1143 is a strain isolated from soil by the present inventors. Its bacteriological properties are given below.

(a) Morphology

Microscopic observation (24° C., bouillon agar medium, cultured for 16 hours)

(1) Size of cell:

rod of 0.4 to 0.5×0.7× to 1.0 $\mu$m.

(2) Pleomorphism

It is a uniform rod. A short chain state of rods connected with each other at the terminals is also observed.

(3) Mobility positive (polar flagella). A chain of two rods rotates.

(4) Spore: No spore is formed.

(5) Gram staining: negative (6) Acid-fast property: negative (b) Growth condition in various media (1) Bouillon agar plate culture Culture at 30° C. for 2 days gives disc-like colonies having a diameter of 1 mm and is pale yellow and oleaginous. The periphery is somewhat undulate but becomes entire after a further time passes.

(2) Bouillon gar slant culture

It grows normally. The bacteria is light yellow and oleaginous and the surface is smooth. No coloration of medium is noted.

(3) liquid culture

Under shake culture, the bacteria exhibits good growth at 30° C., begins to lyse about 5 days after and completely lyses 7 days after to become transparent. In static culture at 30° C., it forms a slight ring on the surface and small white precipitates and becomes slightly turbid as a whole.

(4) Bouillon agar stab culture: (cultured at 30° C. for 7 days)

The bacteria grows slightly along stabs to become filiform.

(5) Litmus milk

The bottom part is slightly reduced, decolored and becomes slightly acidic.

(6) BCP milk

It becomes slightly acidic.

(7) Gelatin stab culture

By culture at 24° C. for 7 days, the surface is liquefied a little bit. (c) Physiological properties (1) Reduction of nitrate: positive (2) Denitrification:

Anaerobic growth is noted but no gas is formed.

(3) MR test: negative (4) VP test: negative (5) Formation of indole: negative (6) Formation of hydrogen sulfide: positive (by lead acetate test paper)

(7) Decomposition of starch: positive (8) Utilization of citrate: negative (9) Utilization of inorganic nitrogen sources:

Ammonium salts are utilized but nitrates are not utilized.

(10) Formation of dye:
A yellow non-diffusible dye is formed.
(11) Urease: negative
(12) Oxidase: negative
(13) Catalase: positive
(14) Growth range:
Temperature at 16° to 38° C. (optimum temperature at about 27° C.)
pH at 5.0 to 9.8 (optimum pH at about 7)
(15) Behavior to oxygen: aerobic
(16) O-F test: no change
(17) Formation of acid and gas from sugars

|    |             | Formation of Acid | Formation of Gas |
|----|-------------|-------------------|------------------|
| 1  | L-arabinose | +                 | −                |
| 2  | D-xylos     | +                 | −                |
| 3  | D-Glucose   | +                 | −                |
| 4  | D-Mannose   | +                 | −                |
| 5  | D-Fructose  | +                 | −                |
| 6  | D-galactose | −                 | −                |
| 7  | Maltose     | +                 | −                |
| 8  | Sucrose     | +                 | −                |
| 9  | Lactose     | +                 | −                |
| 10 | Trehalose   | +                 | −                |
| 11 | D-Sorbitol  | −                 | −                |
| 12 | D-Mannitol  | +                 | −                |
| 13 | Inositol    | −                 | −                |
| 14 | Glycerine   | +                 | −                |
| 15 | Starch      | ±                 | −                |

(d) Other properties
(1) Intracellular accumulation of polyhydroxybutyrate: negative
(2) Production of fluorescent substance: positive
(3) Production of arginine dihydrolase: negative When compared the foregoing taxonomical properties of this strain capable of producing novel L-FDH with the classification in Bergey's Manual of Systematic Bacteriology 1984), Volume 1, this strain is assumed to belong to the genus Pseudomonas since it is gram-negative, aerobic and catalase-positive rods bearing no spore but having polar flagella. The strain is assumed to be akin to *Pseudomonas syringae* or *Pseudomonas viridiflava* since it does not accumulate polyhydroxybutyrate in the cells but produces a fluorescent substance, does not produce arginine dihydrolase and is oxidase-negative. However, the strain is different from these strains in decomposition of starch, denitrification, production of yellow dye, etc. and is believed to be a new strain that is hitherto unknown.

On the foregoing grounds, the strain was named Pseudomonas sp. No. 1143. Pseudomonas sp. No. 1143 has been deposited on Sep. 14, 1988 in the Fermentation Research Institute of the Agency of Industrial Science and Technology of Japan having an address at 1-3, Higashi 1 chome, Isukuba-ski, Ibanski-ken, 305, Japan under accession number 2056 (FERM BP-2056) under the Budapest Treaty.

Next, any of synthetic and natural media may be usable as the medium used in the present invention so long as the medium appropriately contains carbon sources, nitrogen sources, inorganic matters and other nutrients.

As carbon sources, there can be used glucose, lactose, fructose, maltose, glycerin, etc. As the nitrogen sources, there can be preferably used ammonium salts and nitrogenous organic matters such as peptone, casein digestion products, sodium glutamate, yeast extract, etc.

As inorganic matters there can be used salts of sodium, potassium, magnesium, manganese, calcium, iron, etc.

In the present invention, the L-FDH-producing strain is cultured in a medium containing L-fucose, whereby L-FDH can be obtained in a good yield. A preferred example of the culture medium is a medium (pH 7.0) containing 0.3% L-fucose, 0.1% peptone, 0.1% yeast extract, 0.09% monopotassium phosphate, 0.11% dipotassium phosphate, 0.05% magnesium sulfate, and 0.001% ferrous sulfate. When the strain is aerobically cultured in the medium at 30° C. for 24 hours, a production titer becomes 10 to 100 times that in the case of using other carbon sources in place of L-fucose.

The culture temperature is generally in a range of 20° to 35° C., preferably at about 30° C. A pH is generally in a range of 6 to 8, preferably at about 7, at the point when the culture is initiated. When shake or deep spinner culture is carried out for 20 to 40 hours under such conditions, L-FDH is produced and accumulated in the culture.

Since L-FDH is generally present in the cells, the culture is preferably centrifuged or filtered, etc. to isolate the cells alone. The cells are disintegrated in a suitable amount of buffer solution to make the enzyme dissolve, thereby to release the enzyme into the solution.

The cells are disintegrated by physical means using a dynomill, a French press, ultrasonic wave, etc.; chemical means using Triton X-100, sodium lauryl sulfate, EDTA, etc., or enzymatic means using lysozyme, etc., singly or in combination. From the thus obtained solution of disintegrated cells, nucleic acid is removed in a conventional manner and insoluble matters are removed by filtration or centrifugation to give L-FDH. If necessary and desired, L-FDH can be further purified by ordinary means used to isolate and purify enzyme, for example, (1) fractionation with ammonium sulfate, (2) column chromatography using Phenyl Sepharose, (3) column chromatography using DEAE Sephadex, (4) gel filtration by Sephadex G-100, etc. or in combination with other means, if necessary. Thus purified L-FDH can be obtained.

Next, the method for quantitative determination of L-fucose and the kit for quantitative determination in accordance with the present invention are described in detail.

The principle of the quantitative determination in the present invention is shown below.

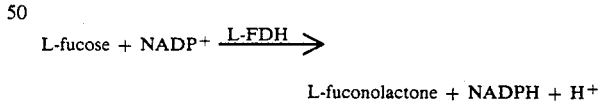

L-fucose + NADP+ $\xrightarrow{\text{L-FDH}}$ L-fuconolactone + NADPH + H+

L-Fucose can be determined by acting L-FDH on L-fucose in a sample, and measuring NADPH produced by known method, for example, by measuring absorbance at 340 nm in the ultraviolet region.

L-FDH of any origin is usable as L-FDH in the present invention as long as it utilizes NADP+ as coenzyme but it is preferred to use L-FDH obtained by culturing a microorganisum, especially a strain selected from bacteria belonging to the genus Pseudomonas.

As the said enzyme-producing bacteria belonging to the genus Pseudomonas, for example, Pseudomonas sp. No. 1143 (FERM BP-2056) is exemplified.

Where the L-FDH described above is reacted with L-fucose in a sample, the reaction is performed under conditions of pH in the range of 7 to 10 and a temperature below 60° C., preferably pH of 8 to 10 and a temperature of 35° to 50° C., generally for approximately 2 to 20 minutes for adjusting the pH, optional buffer solutions that can maintain the pH range described above and does not inhibit the enzyme reaction are used. Examples of the buffer solution which can be advantageously used include potassium phosphate buffer, Trishydrochloride buffer, glycine-sodium hydroxide buffer, sodium carbonate buffer, etc.

For the quantitative determination of NADPH produced by the action of L-FDH, any method may be used but the most typical method involves measurement of absorbance at 340 nm in the ultraviolet region. For the quantitative determination by converting into a dye having an absorption in the visible region, there are known a method which comprises reacting NADPH with phenazine methosulfate and nitro blue tetrazolium and measuring absorbance of the formed diformazan at 570 nm, a method which comprises reacting NADPH with phenazine methosulfate or the corresponding electron transfer or metal ions, causing a color-forming reaction of the formed hydrogen peroxide together with peroxidase and various chromophores and measuring absorbance at a suitable wavelength of each colored matter; etc. The system led to hydrogen peroxide may also be detected by emission of light with luminol. Furthermore, by allowing to coexist with a plurality of oxidation reduction indicators and electron transfers appropriately chosen, the characteristic of their color hues is examined thereby to semi-quantitatively determine L-fucose.

These methods for detection can be used depending upon their characteristics.

In the quantitative determination of L-fucose, it is necessary that L-fucose in a sample be in a free state. Where L-fucose bound as a part of glycoconjugates is assayed, it is necessary to react act α-L-fucosidase, etc. on the conjugates to make L-fucose in a free state. α-L-Fucosidase of any origin may be usable in this case but it is necessary to rapidly cleave the α-L-fucoside bond in the glycoconjugates. Examples of α-L-fucosidase include α-L-fucosidase derived from the genus Aspergillus [J. Biol. Chem., vol. 245, 299-304 (1970)], α-L-fucosidase of sea snail origin [J. Biochem., Vol. 70, 75-78 (1971)] and a-L-fucosidase of animal origin [J. Biol. Chem., Vol. 23-32 (1972)], etc.

The kit for the quantitative determination of L-fucose in accordance with the present invention comprises L-FDH, NADP+ and enzymes and reagents for quantitatively determining NADPH produced, as well as buffer solution reagents for smoothly proceeding these reactions. The reagents and enzymes are prepared into liquid preparations, solid preparations or freeze dried preparations and, depending upon necessity, are dissolved in buffer solutions prior to use, to provide reagents for assay.

L-Fucose is assayed as follows. By directly reacting with a sample containing L-fucose, NADPH is produced. NADPH is assayed as it is or by adding reagents for quantitative determination of NADPH thereto. The assay may be made either by single reagent system or by two reagents system, or further by multi-reagents system.

By using the novel L-FDH of the present invention, L-fucose can be quantitatively determined with good accuracy and useful information for diagnosis of pathological conditions of lung cancer or the like can be obtained. Furthermore according to the present invention, the operation is simple and quantitative assay for L-fucose which is not affected by the co-existing glucose, pyruvate, lactate, lactate dehydrogenase, etc. and is highly accurate can be provided. The present invention is extremely significant in the field of studying glycoconjugates.

Next, the present invention is described by referring to the examples below.

EXAMPLE 1

Pseudomonas sp. No. 1143 (FERM BP-2056), one loopful, was inoculated on 30 ml of sterile seed medium (0.3% L-fucose, 0.1% peptone, 0.1% yeast extract, 0.09% monopotassium phosphate, 0.11% dipotassium phosphate, 0.05% magnesium sulfate, and 0.001% ferrous sulfate, pH 7.0) charged in an Erlenmeyer's flask of 150 ml followed by shake culture at 30° C. The seed culture, 10 ml, was inoculated on 2 liters of medium having the same composition charged in a jar fermenter (manufactured by K. K. IWASHIYA Biological Science) followed by aerial (2 liters/min) spinner (400 rpm) culture at 30° C. for 24 hours. The culture solution was centrifuged at 8,000 rpm for 20 minutes to collect the cells. L-FDH was accumulated in the cell portion.

EXAMPLE 2

Vial cells, 1.1 kg, which had been cultured in a manner similar to Example 1 and the collected cells had been freeze stored at −20° C., were dispersed in 50 liters of 0.02 M potassium phosphate buffer (pH 8.0) (hereafter referred to as standard buffer) and 25 g of lysozyme (manufactured by Nagase & Co., Ltd.). The mixture was allowed to stand at 24° C. for 18 hours. To the mixture were added 1.32 kg of ammonium sulfate and 500 ml of 10% aqueous solution of Triton X-100. The mixture was homogeneously stirred and 80 ml of ethyleneimine polymer aqueous solution (10%, pH 8.0) was then added portionwise to the mixture. The formed precipitates were removed by filtration.

The filtrate was concentrated to 5 liters by a hollow fiber ultrafiltration device (AIL-2011, manufactured by Asahi Chemical Industry Co., Ltd.). After cooling, 1.08 kg of ammonium sulfate was added to the concentrate to dissolve it. After allowing to stand for 2 hours, the formed precipitates were removed by centrifugation at 8,000 rpm for 20 minutes. Furthermore, 0.74 kg of ammonium sulfate was added to the resulting supernatant and the mixture was again allowed to stand for 2 hours. The formed precipitates were collected by centrifugation at 8,000 rpm for 20 minutes. The precipitates were dissolved in 1 liter of standard buffer and 140 g of ammonium sulfate was added to the solution to dissolve. The resulting solution was passed through a column (diameter of 13.3 cm, height of 38 cm) of Phenyl Speharose CL-4B (manufactured by Pharmacia Fine Chemicals Inc., Sweden) which had been previously equilibrated with standard buffer containing 14% ammonium sulfate to adsorb the enzyme to the column. The enzyme was eluted with 50 liters of standard buffer solutions simultaneously having a density gradient (0 to 30%) of ethylene glycol and a reversed density gradient (14 to 0%) of ammonium sulfate.

The active fraction was concentrated to 500 ml with the hollow fiber ultrafiltration device and the concentrate was subjected to dialysis using 3 liters of standard buffer containing 0.1 M potassium chloride. The dialysate was passed through a column (diameter of 6 cm, height of 35 cm) of DEAE-Sephadex A-50, which had been previously equilibrated with standard buffer containing 0.1 M potassium chloride, to adsorb the enzyme to the column. The enzyme was eluted with 10 liters of standard buffer solutions having a density gradient (0.1 to 0.8 M) of potassium chloride. The active fraction was concentrated to 15 ml with a ultrafiltration device (manufactured by Amicon Corp., USA) and 2 ml of the concentrate was passed through a Sephadex G-100 column (diameter of 2.5 cm, height of 100 cm), which had been previously equilibrated with standard buffer containing 0.1 M potassium chloride, to perform gel filtration. The active fractions were collected and concentrated. All of the enzymes were subjected to gel filtration. As the result, 34,000 units of L-fucose dehydrogenase were obtained. As shown in FIG. 5, the enzyme was a preparation showing almost a single band.

EXAMPLE 3

A concentration of L-fucose in a solution was quantitatively determined using the reagents described below by the following method.
1. Reagents

| | |
|---|---|
| 0.1M Potassium phosphate buffer (pH 7.0) | 1.57 ml |
| NADP+ (15 mM) | 0.065 ml |
| L-FDH (44 units/ml) | 0.065 ml |
| Sample solution | 0.30 ml |

2. Method for quantitative determining

A definite amount of each reagent was taken in a test tube. The reagents were reacted at 37° C. for minutes and absorbance was measured at 340 nm. Absorbance obtained in the case of adding the same amount of water instead of the sample and reacting them in a similar manner was deduced from the former absorbance, which was made absorbance of the sample.

Figure 6:
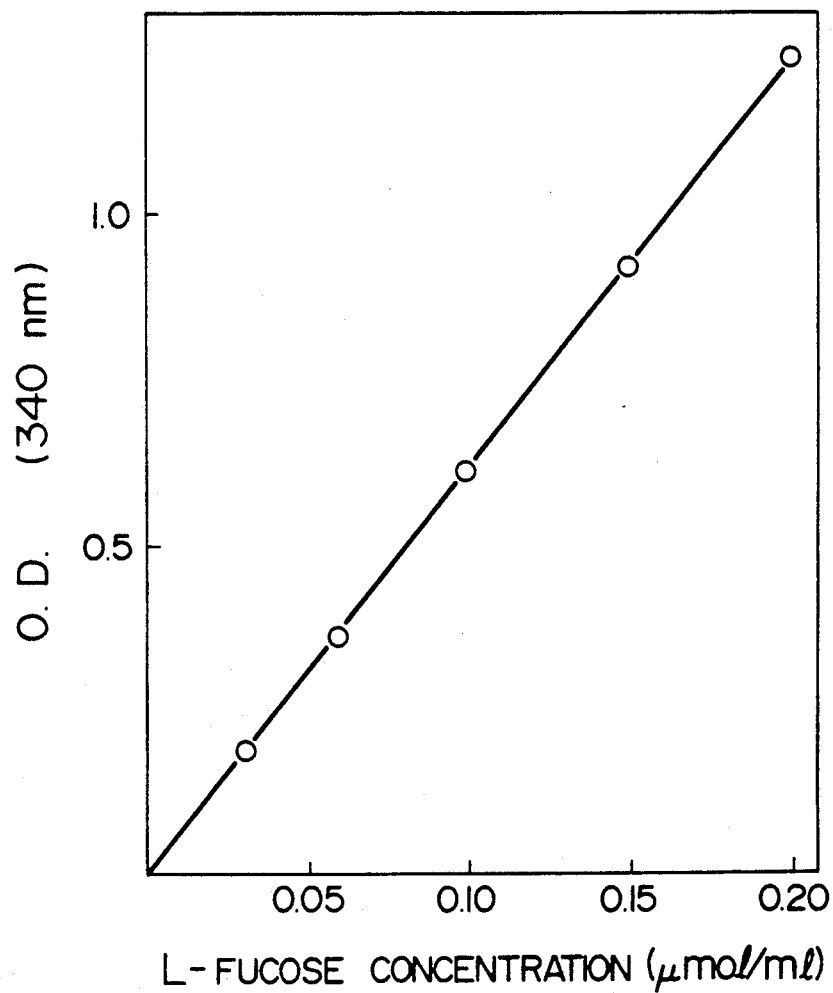
FIG. 6 shows a calibration curve of L-fucose in Example 3.

Separately, L-fucose solutions having known concentrations were treated in a similar manner to obtain a calibration curve. Based on the calibration curve, the concentration of L-fucose was determined. The calibration curve is shown in FIG. 6.

EXAMPLE 4

A concentration of L-fucose in a solution was quantitatively determined using the reagents described below by the following method.
1. Reagents

| | |
|---|---|
| 0.1M Potassium phosphate buffer (pH 8.0) (containing 0.1% Triton X-100) | 150 µl |
| Phenazine methosulfate (1 mg/ml) | 5 µl |
| Nitro blue tetrazolium (10 mg/ml) | 5 µl |
| NADP+ (15 mM) | 15 µl |
| L-FDH (44 units/ml) | 15 µl |
| Sample solution | 10 µl |

2. Method for quantitative determination

A definite amount of each reagent was taken in a test tube. The reagents were reacted at 37° C. for minutes. Then 2.0 ml of 0.3 N hydrochloric acid was added and the mixture was thoroughly mixed.

Absorbance of the formed dye was measured at 570 nm. Absorbance obtained in the case of adding the same amount of water instead of the sample solution and reacting them in a similar manner was deduced from the former absorbance as blank.

Separately, L-fucose solutions having known concentrations were treated in a similar manner to obtain a calibration curve. Based on the calibration curve, the concentration of L-fucose was determined.

EXAMPLE 5

A concentration of L-fucose in 2'-fucosyllactose was quantitatively determined using the reagents described below by the following method.
1. Reagents

| | |
|---|---|
| 0.1M Potassium phosphate buffer (pH 7.0) | 215 µl |
| NADP+ (15 mM) | 15 µl |
| L-FDH (44 units/ml) | 60 µl |
| α-L-fucosidase (bovine epithelium origin) (12 units/ml) | 100 µl |

2. Method for quantitative determination

A definite amount of each reagent was taken in a micro cuvette. After keeping at 37° C. for 5 minutes, 10 µl of each of 0.3, 0.6, 0.9 and 1.2 mM solutions of 2'-fucosyl-lactose was added thereto, respectively. After reacting at 37° C. for 15 minutes, absorbance was measured at 340 nm. Absorbance obtained in the case of adding the same amount of water instead of the 2'-fucosyl-lactose solution and reacting them in a similar manner was deduced from the former absorbance as blank. As the result, a good linear relationship was noted between the added 2'-fucosyl-lactose and increment of the absorbance at 340 nm.

What is claimed is:

1. A substantially pure L-fucose dehydrogenase characterized in that
    said L-fucose dehydrogenase acts by withdrawing hydrogen from L-fucose thereby converting it into L-fuconolactone and at the same time, reducing coenzyme NADP+ to NADPH wherein the activity of said L-fucose dehydrogenase toward D-arabinose and NAD+, respectively; and
    when using Tris-imidazole-sodium acetate buffer solution the optimum pH for activity of said L-fucose dehydrogenase is in the range of 9.0 to 10.0 and the stable pH range is between 8.0 and 10.5.

2. A process for producing an L-fucose dehydrogenase according to clam 1, utilizing NADP+ as coenzyme which comprises culturing in medium an L-fucose dehydrogenase-producing strain belonging to the genus Pseudomonas and collecting formed L-fucose dehydrogenase from the culture.

3. A method according to claim 2, wherein the L-fucose dehydrogenase-producing strain is Pseudomonas sp. No. 1143 (FERM BP-2056).

4. A method for quantitive determination of L-fucose which comprises reacting a sample containing L-fucose with an L-fucose dehydrogenase according to claim 1, requiring NADP+ as coenzyme and measuring NADPH formed.

5. A method for quantitive determination of L-fucose which comprises reacting a sample containing L-fucose with L-fucosidase and an L-fucose dehydrogenase according to claim 1, requiring NADP+ as coenzyme sequentially or simultaneously and measuring NADPH formed.

6. A kit for quantitive determination of L-fucose comprising an L-fucose dehydrogenase according to claim 1, NADP+ and a buffer solution.

* * * * *